(12) United States Patent
Tothne Kovesdi

(10) Patent No.: US 9,033,860 B2
(45) Date of Patent: May 19, 2015

(54) MAGNETIC DEVICE FOR THERAPEUTIC PURPOSE

(71) Applicant: Natalia Tothne Kovesdi, Budapest (HU)

(72) Inventor: Natalia Tothne Kovesdi, Budapest (HU)

(*) Notice: Subject to any disclaimer, the term of this patent is extended or adjusted under 35 U.S.C. 154(b) by 277 days.

(21) Appl. No.: 13/766,836

(22) Filed: Feb. 14, 2013

(65) Prior Publication Data

US 2013/0211180 A1    Aug. 15, 2013

Related U.S. Application Data

(60) Provisional application No. 61/598,917, filed on Feb. 15, 2012.

(51) Int. Cl.
*A61N 2/00* (2006.01)
*A61N 2/06* (2006.01)
*A61N 5/06* (2006.01)

(52) U.S. Cl.
CPC *A61N 2/002* (2013.01); *A61N 2/06* (2013.01); *A61N 5/0613* (2013.01); *A61N 2005/0644* (2013.01); *A61N 2005/066* (2013.01)

(58) Field of Classification Search
USPC ....................................... 600/9–15
See application file for complete search history.

(56) References Cited

U.S. PATENT DOCUMENTS

| | | | | |
|---|---|---|---|---|
| 5,451,199 A * | 9/1995 | Kim et al. | ........................... | 600/9 |
| 6,383,129 B1 * | 5/2002 | Ardizzone et al. | ................. | 600/9 |
| 6,544,164 B1 * | 4/2003 | Fan | .................... | 600/15 |
| 6,652,446 B1 * | 11/2003 | Bove et al. | ....................... | 600/15 |
| 7,309,309 B2 * | 12/2007 | Wang et al. | ...................... | 600/14 |

* cited by examiner

*Primary Examiner* — John Lacyk

(57) ABSTRACT

A combined magnetic and irradiating device for therapeutic purposes applies infrared rays and magnetic force. The device includes a shell designed to be gripped by a user, including an outer surface shaped by at least three flat areas, and an inner bore-hole formed inside the shell for receiving first and second magnets in close connection with each other. Both magnets have north and south pole surfaces and an axis, respectively, aligned with each other, and said north pole surface of the first magnet is exposed on a surface of the shell. Windows having an inner rim are arranged on each flat area of the shell. Said close connection is established between the south pole surface of the first magnet and north pole surface of the second magnet. At least one infrared radiating tablet is fixed in said window and abutted against said rim by a clamp placed inside said bore-hole.

8 Claims, 6 Drawing Sheets

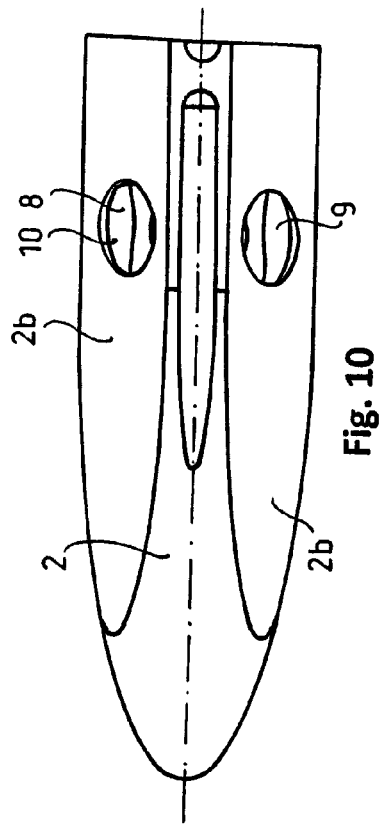
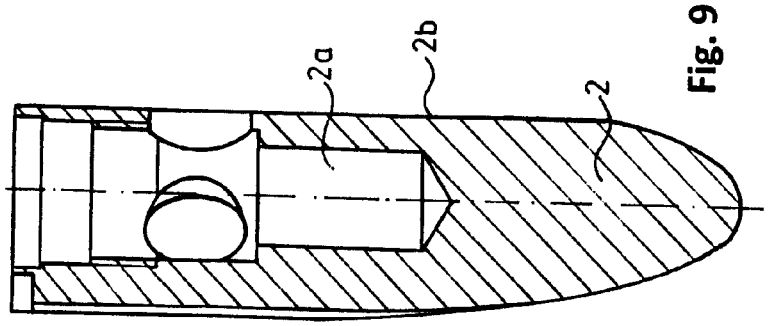
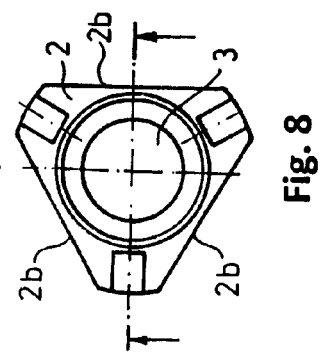
Fig. 9
Fig. 8
Fig. 10

MAGNETIC DEVICE FOR THERAPEUTIC PURPOSE

FIELD OF THE INVENTION

The present invention relates to a combined magnetic and irradiating device for therapeutic purpose applying infrared rays and magnetic force for pain relieving, antiphlogisting and improving feeling of general condition.

BACKGROUND ART

A reduction of the magnetism of the earth is a scientific fact not to be proved here, and according to observations in different places of the earth it ranges between 0.4 and 0.8 G, and it has been further reducing by 5% during the last hundred years. At the same time several publications reporting on beneficial effects of magnetic field are known in the literature, e.g a study of Dr. Kyoichi Nakagawa a rheumatologist, director of the Isuzu Hospital in Tokyo, Japan, reporting a research on treatments of 11,648 patients by magnetic field (Japan Medical Journal 2745:1-11, 1976.) He found that 91% of people felt the magnetic field helpful in relieving different kind of pain. Dr. Nakagawa stated that degradation of the earth's magnetic field is responsible for the "Magnetic Deficiency Syndrome", as he calls it. According to Nakagawa by applying a static magnetic field of approximately 850 G the relief of many distressing biological symptoms occurs.

Furthermore, it is widely known that the far infrared radiation is absorbed by the skin in a rate of more that 93%, and it has a very well documented beneficial effect to the circulation and also has a pain relieving action and improves the conveying capacity of the blood.

Magnetic therapy has a wide range of literature and its application is of a common occurrence in medical praxis, consequently, its effectiveness is not to be proved, but the devices designed for that purpose are not apt for everyday use as being relatively large appliances which cannot be portable in a pocket, at least not comfortably. Moreover, these devices may require supply sources and need e.g. battery change if it went flat.

In order to overcome this problem U.S. Patent Application 2008/0319358 A1 discloses a therapeutic massage tool comprising a handle having a cylinder provided for holding, a barrel hole going through the cylinder, a first rim formed at end of the cylinder; a first barrel having a barrel body inserted into the barrel hole of the handle, a chamber formed concaved on the barrel body, a barrel end connected to the barrel body, a rim stopped against the first rim of the handle, a fitting hole opened from bottom of the chamber through the barrel end; a toe having a shoulder received inside the chamber of the first barrel, a toe post inserted to the fitting hole of the first barrel, a toe head extended outside the barrel end of the first barrel; a second barrel having a barrel body inserted into the barrel hole of the handle, a barrel end connected to the barrel body; a magnet received in the chamber of the first barrel. This massage tool has at least one magnet improving blood circulation; it is tiny and light-weight.

It seems, however, that only the effect of north magnetic pole is beneficial and long lasting, and when both magnetic poles being administered to a patient simultaneously unpleasant effects appear (Philpott, V'. H. and Taplin, S, L. Biomagnetic Handbook: Today's Introduction to the Energy Medicine of Tomorrow. Choctaw, Okla.: Enviro-Tech Products, 1990, pp. 23 and 24). Using the magnetic north pole only, the conveying capacity of the blood increases, that is both the delivery of oxygen and nutrients to the cells and removal the wastes therefrom become more effective and faster. This way, in contrast with "both pole" magnetic therapy, the "north pole" magnetic therapy results in occurring beneficial processes in the body and it is really suitable for improving general condition of the patient.

Therefore, the tool disclosed in the U.S. Patent Application 2008/0319358 A1 has serious disadvantages. The magnet is a very long one, consequently its magnetic field lines are also long parallelly to the axis of the tool. The effectiveness of such a device depends on the strength of that part of the magnetic field, which permeates the skin. Such long magnetic field lines have substantial loss and the magnetic field permeating the skin of the human body involves only a restricted part of the whole magnetic field of the magnet. Therefore, the tool disclosed in U.S. Patent Application 2008/0319358 A1 could be effective only when its magnet was very strong, even far strongest than a magnet necessary to be useful, and the production costs of such strong and big magnets are very high, even the magnet is assembled by placing several less magnets side by side. Further, the magnetic field lines exiting the south pole of this tool can freely penetrate the skin of a user deteriorating the useful effects of the north pole, as stated above.

Therefore, the object of the invention is to provide a magnetic device for therapeutic purpose having low production costs and high effectiveness by allowing the flux-lines of the north magnetic pole only to be contacted the patient's body.

A further object of the present invention is to provide a combined magnetic and irradiating device for therapeutic purpose applying infrared rays and magnetic force for pain relieving, antiphlogisting, and repairing feeling of general condition.

SUMMARY OF THE INVENTION

To achieve above objects a combined magnetic and irradiating device is provided for therapeutic purpose applying infrared rays and magnetic force for pain relieving, antiphlogisting and improving feeling of general condition, said device consists of:

a shell designed to be gripped by a user, the outer surface of the shell is shaped by at least three flat areas, and an inner bore-hole is formed inside the shell for receiving a first magnet and a second magnet in close connection with each other, both magnets having north and south pole surfaces and an axis, respectively, aligned with each other, and said north pole surface of the first magnet is exposed on a surface of the shell, and windows having an inner rim are arranged on each flat area of the shell, a closure apt to be releasably connected to the shell, and having a bolt fixed thereinside with a flat end exposed in a surface of the closure, wherein said close connection is established between the south pole surface of the first magnet and north pole surface of the second magnet, and in a connected state of the shell and the closure the axis of the magnets are perpendicular to the flat end of the bolt, at least one infrared radiating tablet fixed in said window and abutted against said rim by a clamp placed inside said bore-hole.

Said magnets preferably have a residual induction of at least 5000 G together, and are retained in close connection by a magnet holder inserted in said bore-hole.

The shell and said closure are advantageously made of Al—Mg alloy, preferably AlMgSi alloy.

In a preferred embodiment of the device according to the invention the closure can be replaced by a cap provided by a magnet having residual induction of at least 8000 G.

All flux lines of the magnets are extended wholly inside the shell, and all flux lines of the magnets are extended wholly inside the shell and the closure, when said closure is connected to the shell.

Said flat areas are preferably formed at an angle of 60° to each other.

BRIEF DESCRIPTION OF THE DRAWINGS

The invention is further disclosed by details referring to the attached drawings, in which.

DETAILED DESCRIPTION OF THE INVENTION

Figure 1:
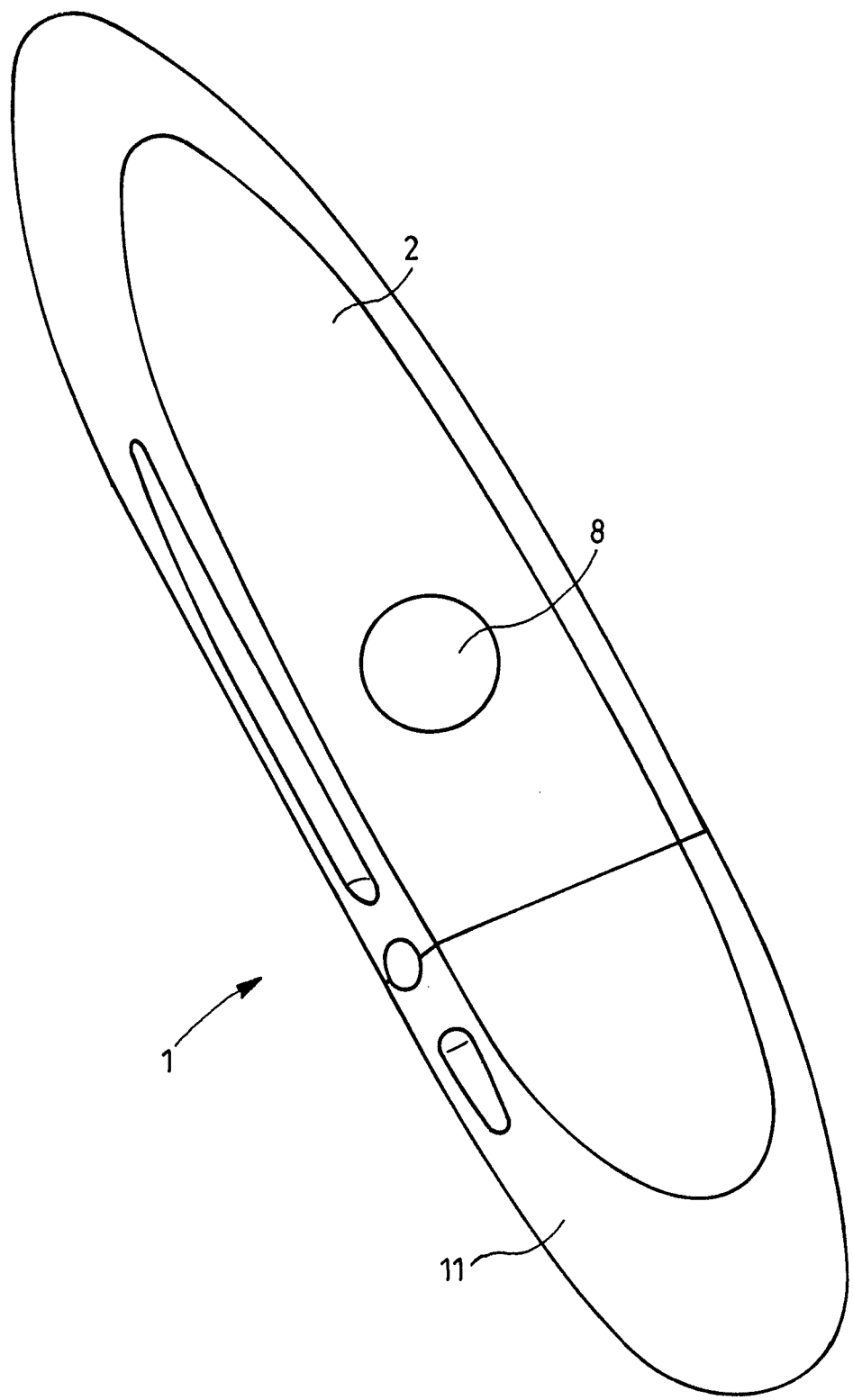
FIG. 1. is a perspective view of the device according to the invention.

FIG. 1. is perspective view of a combined magnetic and irradiating device 1 according to the invention. The device 1 consists of a shell 2 to be gripped by a user and a closure 11 releasably connected to the shell.

Figure 2:
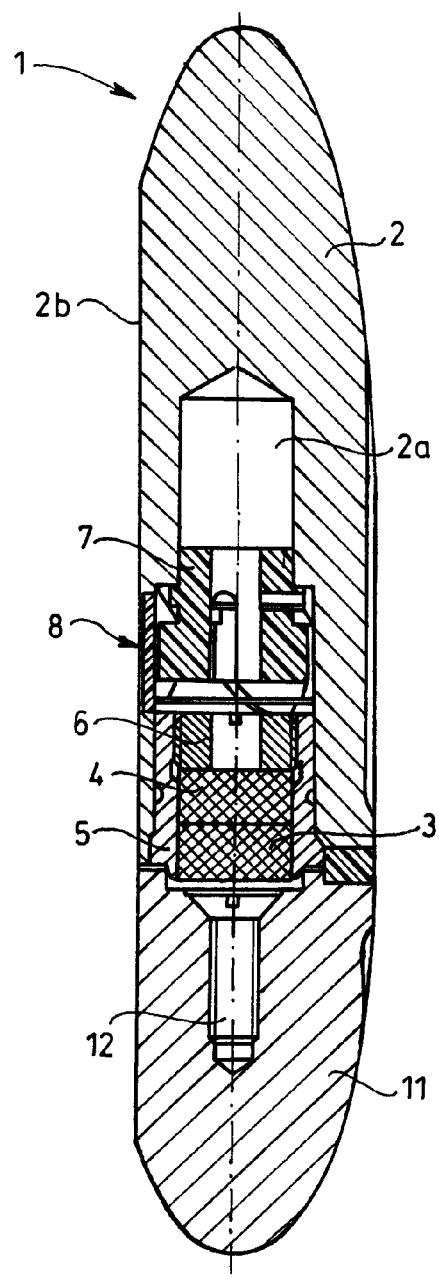
FIG. 2. is an elevational cross sectional view of a combined magnetic and irradiating device according to the present invention, in assembled state, FIG. 3. is a top side view of the device 1, FIG. 4. is an elevational view of the magnet holder, FIG. 5. is a top side view of the closure, FIG. 6. is a cross sectional view of the closure, FIG. 7. is a side view of the closure, FIG. 8. is a bottom view of the shell, FIG. 9. is a is a cross sectional view of the shell, FIG. 10. is a side view of the shell, and FIG. 11. is an elevational view of a magnet to be used according to the invention.
Figure 11:
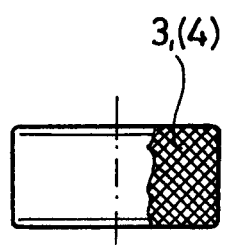

FIG. 2. generally depicts an elevational cross sectional view of a combined magnetic and irradiating device 1 for therapeutic purpose applying infrared rays and magnetic force according to the present invention. The device 1 has a shell 2 designed to be gripped by the user and its outer surface is shaped by three flat areas 2b in such a way, that the cross section of the shell forms a regular triangle with rounded apices, as clearly shown in FIG. 8. An inner borehole 2a is formed inside the otherwise solid shell for receiving a first permanent magnet 3 and a second permanent magnet 4 (FIG. 11) in close connection with each other (FIG. 2), such that their opposite poles are contacted. The magnets 3,4 are relatively little but strong magnets 3,4, made of e.g. AlNiCo or rare earth metal alloy containing Sm, etc., the residual induction ($B_r$) of the overall magnetic field created is at least 5000 Gauss.

Figure 4:
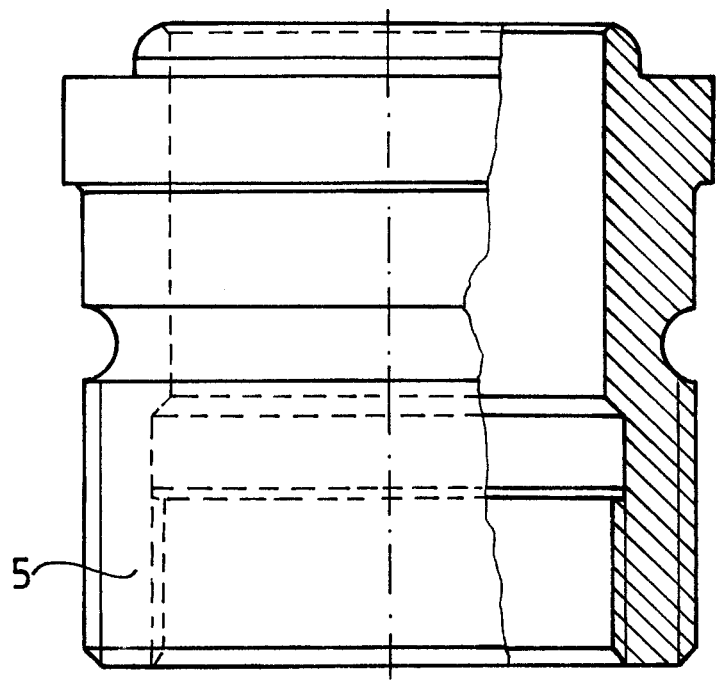

The shell 2 (FIGS. 8,9 and 10) is made of metal e.g an Al—Mg alloy, preferably AlMgSi alloy shielding the magnetic field of the magnets 3,4 at the side of the shell, but leaving magnetically open the pole of the magnet 3 being not in contact with the magnet 4. The magnets 3,4 are embedded advantageously in a magnet holder 5 having a fixing part 6 inside securing the magnets 3,4 within the magnet holder 5 enhancing easy assembly of the device 1, that is the magnet holder 5 provided previously by magnets 3,4 and said fixing part 6 can be pushed into the borehole 2a during production. The magnet holder 5 retaining magnets 3,4 in the proper position inside the borehole 2a of the shell 2 is depicted in FIG. 4.

Figure 3:
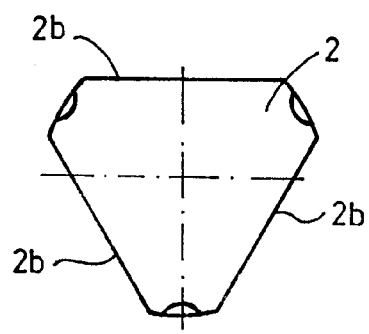

A clamp 7 is further arranged in the borehole 2a for outwardly pushing infrared radiating tablets 8 against cylindrical rims 9 of three tablet windows 10 formed on each flat areas 2b of the shell 2 (FIG. 10). Infrared tablets 8 are preferably so called FIR (Far Infrared) bioceramic fiber pastilles having a feature of radiating infrared radiation for a long time if they had been previously irradiated by infrared radiation. Since the FIR tablets 8 affect in a best way by engaging with the skin, these tablets 8 are arranged in such a way that each finger of the user gripping the device 1 according to the invention must be contacted the surface of a tablet 8, and then the beams of infrared radiation enter the body through this area of the skin. The flat areas 2b are formed preferably at an angle of 60° to each other to provide a comfortable gripping possibility to the user, as it can be seen clearly in FIG. 3, a top side view of the device 1.

We have found that a "north pole" embodiment of the device according to the invention, that is the open pole of the magnet 3 is a north pole, is suitable for providing adequate magnetic field to the human body for a period of half an hour. We have also found that a magnetic field of more than or at least equal to 5000 G in strength has a remarkable pain relieving and antiphlogisting effect.

Figure 6:
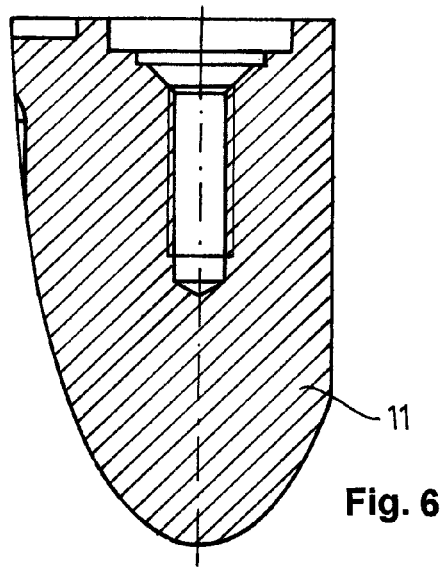
Figure 5:
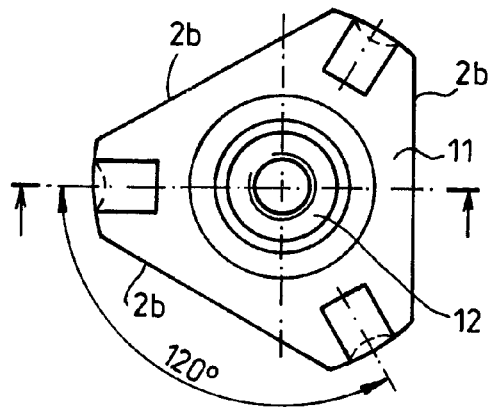
Figure 7:
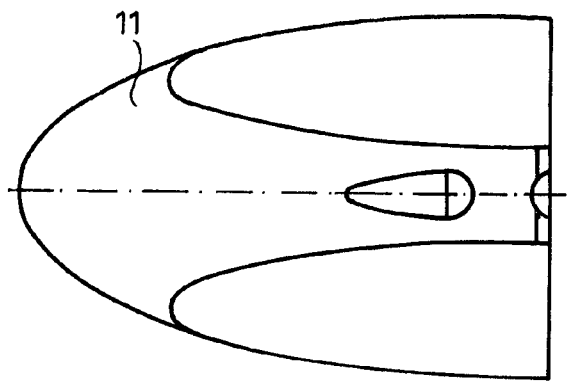
Figure 12:
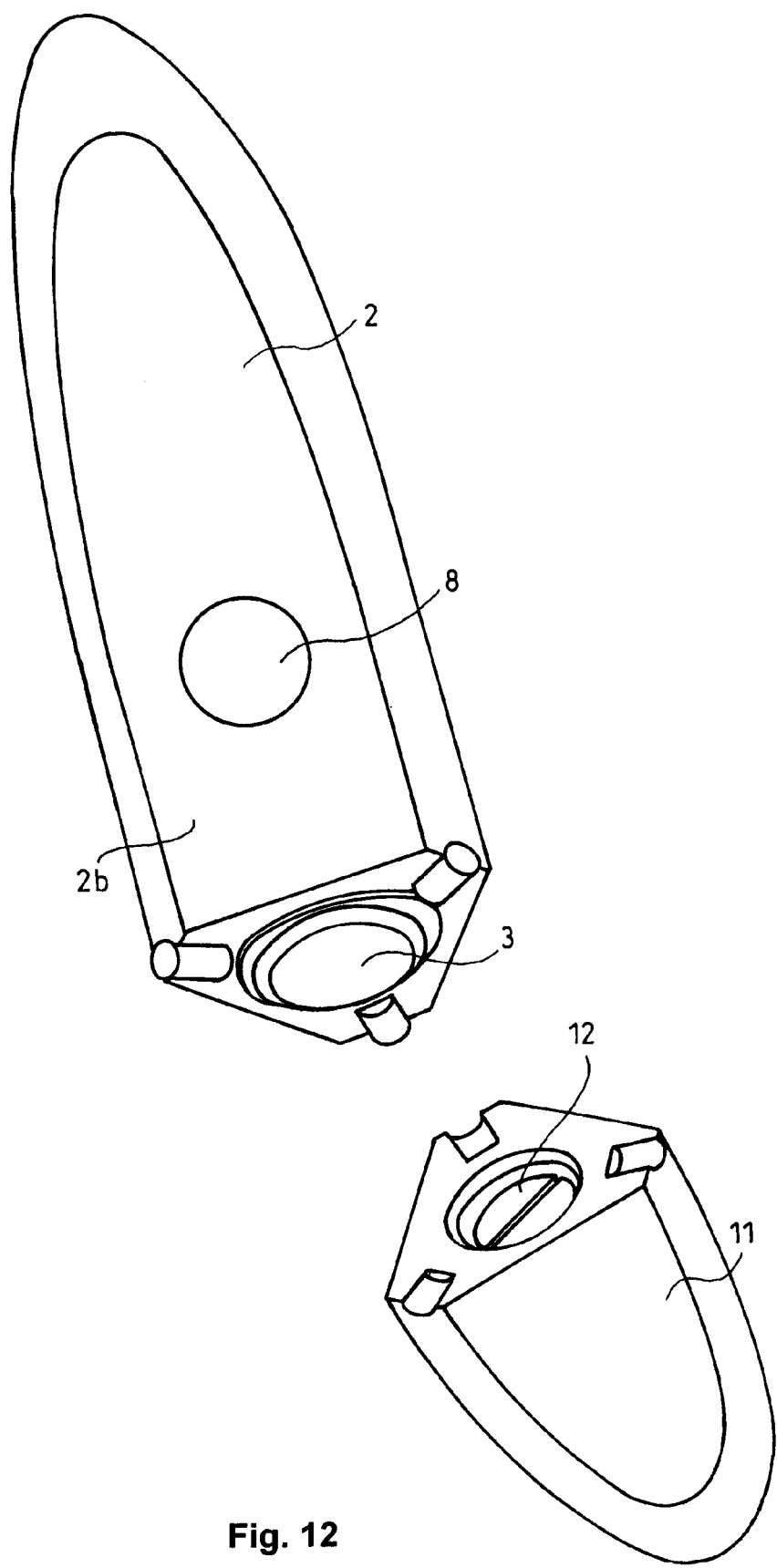
FIG. 12. is a perspective view of the device according to the invention, with separated closure and shell.

The magnets 3,4 can be further shielded at the open pole of the magnet 3 by means of a closure 11 (FIGS. 5, 6 and 7) releasably mounted to the shell 2 and containing a bolt 12 to collect the magnetic field lines in order to not exit the device 1 at the time of lay-up, because the magnetic field strength of at least 5000 G is very strong to be used incidentally and without control. The closure 11 can be made of the same material as the shell 2 e.g. made of Al—Mg alloy, preferably AlMgSi alloy. Due to the shape and material of the shell 2 and the closure 11 all flux lines of the magnets 1,2 are extended wholly inside the shell 2 and the closure if the latter is connected perfectly to the shell. If, however, the closure is removed (FIG. 12), the flux lines exit the shell 2 around the magnet 3 only and can be penetrated the skin of a patient.

The closure 11 can be replaced by a cap provided by a magnet having residual induction of at least 8000 G, not shown in the drawings, in order to improve the therapeutical effect of the device 1.

The device 1 according to the invention can be used by a user to the own body taking a user's manual as a basis. The fingers, preferably the index-finger, middle-finger and the thumb, of the user can be placed on the FIR tablets 8, respectively, and contacting with a skin surface area (i) felt aching or (ii) inflamed by the end of the device with the open magnet 3 pole.

The device 1 according to the invention may not applicable by users, to which the magnetic therapy is contra-indicated, or having implanted devices as a pacemaker, automatic insulin dispenser etc., or those having implanted means made of metals. It is confined to apply by pregnant women, nursing mothers and in case of carcinoma.

The device 1 according to the invention has the advantage of portability, being small sized, it does not require external power source, and the benefits of "north pole" magnetic therapy are completed by positive physiological effects of acupressure and long wave range infrared radiation. Moreover, it is apt for being in a pocket of the user who itself can compensate magnetic energy that he/she may not acquire from the magnetic field of the earth because of permanent reduction thereof.

The present invention has been disclosed above by a specific embodiment thereof. Nevertheless, the person skilled in the art can apply other forms or shapes of the device according to the present invention in order to better exploit advantages thereof, which embodiments, however, are included in the scope of the attached claims.

The invention claimed is:

1. A combined magnetic and irradiating device (1) for therapeutic purpose applying infrared rays and magnetic force for pain relieving, antiphlogisting and improving feeling of general condition, said device consists of:
 a shell (2) designed to be gripped by a user, the outer surface of the shell (2) is shaped by at least three flat areas (2*b*), and an inner bore-hole (2*a*) is formed inside the shell (2) for receiving a first magnet (3) and a second magnet (4) in close connection with each other, both magnets (3,4) having north and south pole surfaces and an axis (A1, A2), respectively, aligned with each other, and said north pole surface of the first magnet (3) is exposed on a surface of the shell (2), and windows (10) having an inner rim (9) are arranged on each flat area (2*b*) of the shell (2),
 a closure (11) apt to be releasably connected to the shell (2), and having a bolt (12) fixed thereinside with a flat end exposed in a surface (11*a*) of the closure (11),
wherein said close connection is established between the south pole surface of the first magnet (3) and north pole surface of the second magnet (4), and in a connected state of the shell (2) and the closure (11) the axis (A1, A2) of the magnets (3,4) are perpendicular to the flat end of the bolt (12), at least one infrared radiating tablet (8) fixed in said window (10) and abutted against said rim (9) by a clamp (7) placed inside said bore-hole (2*a*).

2. The combined magnetic and irradiating device (1) according to claim 1, wherein said magnets (3,4) have a residual induction ($B_r$) of at least 5000 G together.

3. The combined magnetic and irradiating device (1) according to claim 1, wherein said magnets (3,4) are retained in close connection by a magnet holder (5) inserted in said bore-hole (2*a*).

4. The combined magnetic and irradiating device (1) according to claim 1, wherein said shell (2) and said closure (11) are made of Al—Mg alloy, preferably AlMgSi alloy.

5. The combined magnetic and irradiating device (1) according to claim 1, wherein said closure (11) can be replaced by a cap provided by a magnet having residual induction of at least 8000 G.

6. The combined magnetic and irradiating device (1) according to claim 1, wherein all flux lines of the magnets (1,2) are extended wholly inside the shell (2).

7. The combined magnetic and irradiating device (1) according to claim 1, wherein all flux lines of the magnets (1,2) are extended wholly inside the shell (2) and the closure (11), when said closure (11) is connected to the shell (2).

8. The combined magnetic and irradiating device (1) according to claim 1, wherein said flat areas (10) are formed at an angle of 60° to each other.

* * * * *